United States Patent [19]
Fogarty et al.

[11] Patent Number: 6,007,552
[45] Date of Patent: Dec. 28, 1999

[54] VASCULAR CLAMPS AND SURGICAL RETRACTORS WITH DIRECTIONAL FILAMENTS FOR TISSUE ENGAGEMENT

[75] Inventors: Thomas J. Fogarty; George D. Hermann, both of Portola Valley; Joshua S. Whittemore, Mountain View; Thomas A. Howell, Palo Alto, all of Calif.

[73] Assignee: Minumys, Cupertino, Calif.

[21] Appl. No.: 08/993,076

[22] Filed: Dec. 18, 1997

[51] Int. Cl.⁶ .................................................. A61B 17/00
[52] U.S. Cl. ............................................................ 606/157
[58] Field of Search ........................... 606/207, 205–206, 606/144, 148, 151, 142, 208–210, 139, 167, 157, 158, 51, 52; 24/521, 522, 518; 30/137

[56] References Cited

U.S. PATENT DOCUMENTS

| | | |
|---|---|---|
| 2,743,726 | 5/1956 | Grieshaber . |
| 3,503,396 | 3/1970 | Pierie et al. . |
| 3,503,397 | 3/1970 | Fogarty et al. . |
| 3,503,398 | 3/1970 | Fogarty et al. . |
| 3,746,002 | 7/1973 | Haller . |
| 3,880,166 | 4/1975 | Fogarty . |
| 3,993,076 | 11/1976 | Fogarty . |
| 4,548,202 | 10/1985 | Duncan . |
| 4,611,593 | 9/1986 | Fogarty et al. . |
| 4,821,719 | 4/1989 | Fogarty ................................... 606/157 |
| 4,955,897 | 9/1990 | Ship ........................................ 606/210 |
| 5,171,253 | 12/1992 | Klieman ................................. 606/158 |
| 5,535,756 | 7/1996 | Parasher . |
| 5,591,182 | 1/1997 | Johnson ................................. 606/151 |

FOREIGN PATENT DOCUMENTS

| | | | |
|---|---|---|---|
| 0 490 301 A1 | 12/1991 | European Pat. Off. | ........ A61B 17/28 |
| 65626 | 8/1913 | Switzerland | ........................... 606/207 |
| WO 98/33437 | 8/1998 | WIPO | .............................. A61B 17/00 |

*Primary Examiner*—Michael Buiz
*Assistant Examiner*—Vikki Trinh
*Attorney, Agent, or Firm*—Limbach & Limbach L.L.P.

[57] ABSTRACT

A surgical clamp or tissue retractor is disclosed having gripping surfaces from which extend resilient filaments. The distal ends of some of the resilient filaments abut against the engaged vessel or tissue to restrict movement of the vessel or tissue relative to the gripping surfaces. In the preferred embodiment, the resilient filaments are arranged in rows and oriented at particular angles relative to the gripping surfaces.

34 Claims, 17 Drawing Sheets

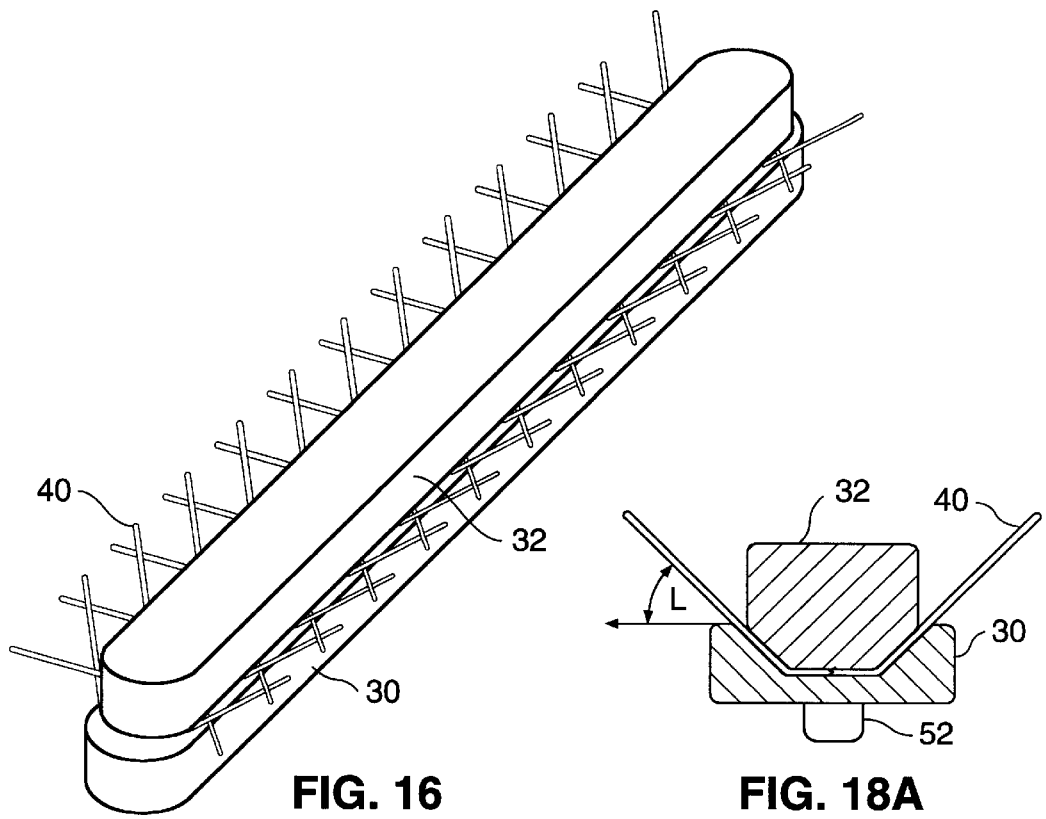
FIG. 16  FIG. 18A
FIG. 18B  FIG. 18C  FIG. 18D
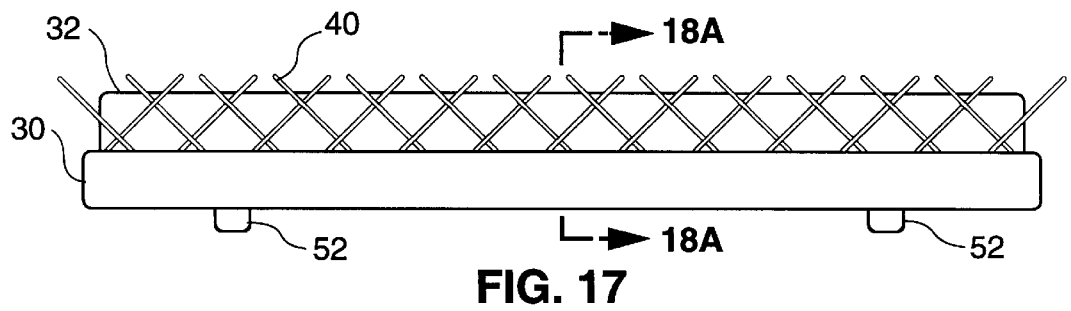
FIG. 17

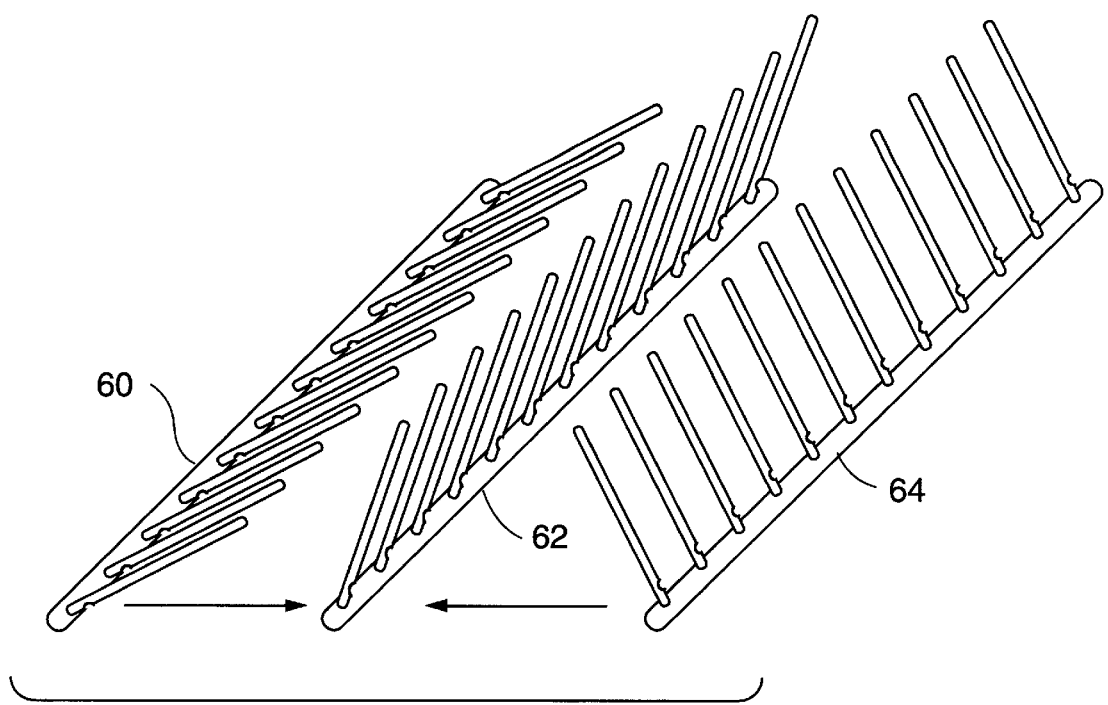
FIG. 24
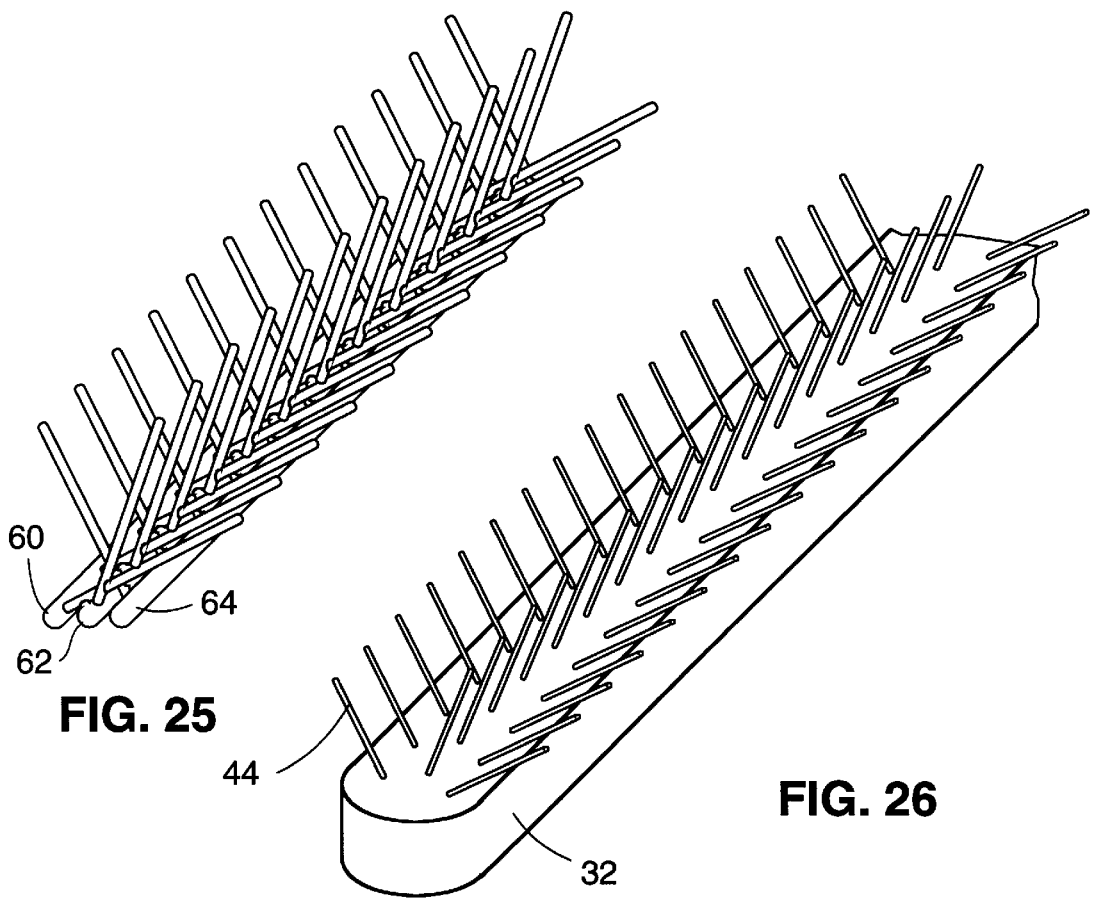
FIG. 25
FIG. 26

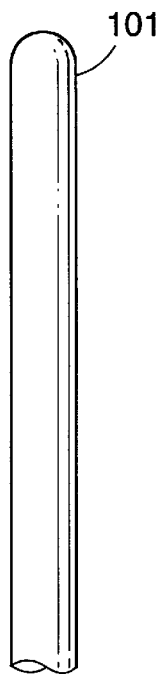 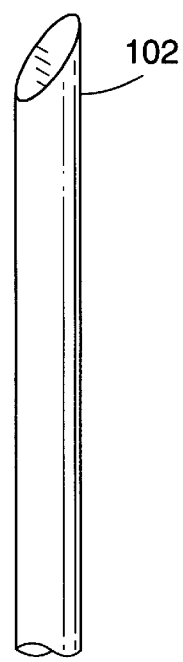 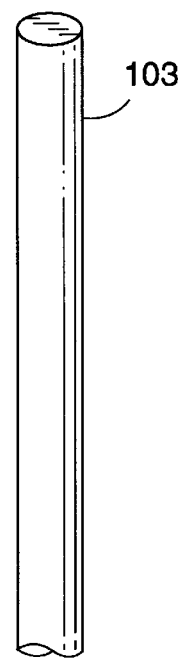 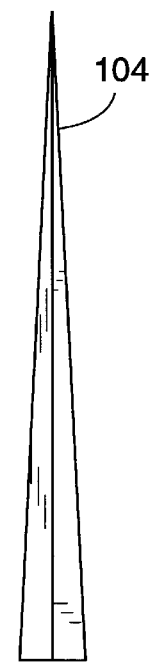 
FIG. 32A    FIG. 32B    FIG. 32C    FIG. 32D    FIG. 32E
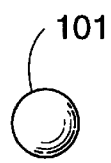 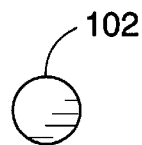 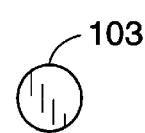 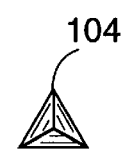 
FIG. 33A    FIG. 33B    FIG. 33C    FIG. 33D    FIG. 33E

VASCULAR CLAMPS AND SURGICAL RETRACTORS WITH DIRECTIONAL FILAMENTS FOR TISSUE ENGAGEMENT

BACKGROUND OF THE INVENTION

1. Field of the Invention

The present invention relates generally to a surgical clamp for occluding a vessel or other tubular structure or for grasping and retaining other body tissue, and to a surgical retractor for retracting tissue at a surgical incision site. More particularly, the invention relates to a surgical clamp or surgical retractor which includes resilient filaments that abut against a vessel or tissue to resist movement of the vessel or tissue relative to the clamp or retractor.

2. Description of the Related Art

Instruments for occluding blood vessels during surgery, such as conventional metal or rigid surgical clamps or clips, are well known. However, such instruments are known to cause trauma to the clamped vessel at the clamping site. A number of atraumatic instruments have been developed for reducing or eliminating the trauma to a vessel during occlusion of the vessel. U.S. Pat. No. 3,993,076 to Fogarty, et al. describes a device whereby a vessel is occluded by using a resilient tape to press a vessel against a resilient pad. However, this device suffers from the disadvantage that it slips easily. For example, the pulsations of an occluded artery can tend to force the device off of its clamped position on the occluded artery. Conventional surgical clamps have also been adapted to include jaw surfaces containing resilient members or pads. These devices likewise are prone to slipping off of the clamped vessel. This can be especially problematic in situations where, due to obstructions, a vessel has been clamped with only the distal tips of the clamp jaws. In such situations, the vessel can be especially prone to slipping in the direction of the distal tips.

Other attempts have been made to atraumatically occlude a vessel in a secure fashion. U.S. Pat. No. 3,746,002 to Haller describes a vascular clamp with resilient gripping members located on the jaws. A plurality of pin members are embedded within the gripping members, the pin members of a length such that when a vessel is clamped between the members, the resilient material deflects to accommodate the vessel, exposing the pin members which grippingly engage the outer layer of the vessel, thus securing the vessel to the gripping member. While the Haller device is less traumatic to a vessel than other occlusion devices, it nevertheless has the disadvantage of traumatizing the outer layer of the vessel.

U.S. Pat. No. 4,821,719 to Fogarty describes a vascular clamp device containing resilient pads with Velcro-like hooks. The hooks interact with the external adventitial layer of the vessel forming a cohesive-adhesive relationship with the vessel similar to the bonding of Velcro materials. While this device offers a less traumatic way to occlude a vessel, the cohesive-adhesive nature of the bond can result in the removal of some of the adventitial layer of the vessel when disengaging the device.

There is thus a need for a surgical clamp which atraumatically occludes vessels while avoiding the disadvantages previously associated with existing surgical clamps or occlusion devices.

Likewise, conventional tissue retractors are well known which retract tissue at a surgical incision site to provide a surgeon visual and mechanical access to the interior of a patient's body. These tissue retractors employ rigid gripping members, usually of metal, to grip, retract, and retain all forms of body tissue, e.g., bone, skin, fat, or muscle, at the incision site. The disadvantage of such retractors are twofold. First, the rigid gripping members, due to their rigidity, cause trauma to the retained tissues. Second, the gripping members are generally prone to slippage, both laterally, along the sides of the incision, and upwardly out of the incision and away from the patient's body.

Thus, there is also a need for a surgical retractor that atraumatically, yet securely, retracts and retains tissue at a surgical incision site.

SUMMARY OF THE INVENTION

It is an object of the present invention to provide a surgical clamp or other occlusion device, or a surgical retractor, having a gripping surface and an array of resilient filaments extending at acute angles relative to the surface for engagement with vessels or tissue. The filaments terminate in free distal ends which abut against the engaged vessel or tissue to resist and restrict movement of the engaged vessel or tissue in a direction opposed to the orientation of the filaments. The filaments themselves can also be resiliently flexible so as to cushion the engaged vessel or tissue.

In the case of a surgical clamp according to the present invention, the filaments are located on opposing jaws of a surgical clamp. When the jaws are moved toward one another to engage a vessel, some of the filaments, based on their angle of orientation in relation to the vessel, will abut against the vessel and impart a resistive force against the vessel along the direction of the filament. When the jaws of the surgical clamp are partially or fully engaged with the vessel, filaments of the lower jaw push or lever the vessel upward toward the upper jaw, while at the same time filaments of the upper jaw push or lever the vessel downward toward the lower jaw. This levering action of the filaments secures against movement of the vessel in a direction generally opposed to the orientation of particular filaments.

In one embodiment of the invention, the filaments can extend directly from the surface, which itself can be resiliently flexible. In this embodiment, when the jaws are moved toward one another to engage a vessel, some of the filaments, based on their angle of orientation in relation to the vessel, will be pressed flat against the surface which will itself deflect to accommodate the vessel in atraumatic fashion. In an alternative embodiment, the filaments can extend from along the sides of the resilient surface and the distal ends of the filaments can terminate at positions even with, above, or below the level of the surface. In this embodiment, the surface can deflect to atraumatically engage the vessel while the filaments are likewise engaging the vessel and resisting movement of the vessel in a direction opposed to the orientation of the filaments. Where the distal ends of the filaments terminate at a position below the level of the surface, the surface will deflect to a position where both the surface and the filaments will engage the vessel.

In another embodiment of the invention, the filaments can be oriented as discussed above to resist movement of the vessel in the direction of the distal ends of the surgical clamp jaws. Such an orientation is especially advantageous where, due to obstructions, a surgeon can only access and clamp a vessel with the distal tips of the surgical clamp jaws. With a conventional clamp, the vessel can slip from the clamp in the direction of the distal tips. In the above embodiment of the present invention, however, slippage of the vessel will favor the direction back toward the proximal ends of the surgical clamp jaws, thereby retaining the vessel in a clamped condition.

In another embodiment of the invention, the filaments of the upper and lower jaws of the surgical clamp are oriented to resist movement of a clamped vessel towards either the distal or the proximal ends of the jaws. The filaments can also be oriented to resist movement of a clamped vessel in a direction perpendicular to the jaws.

A surgical retractor according to the present invention likewise uses resilient surfaces with resilient filaments that engage and retract tissue. When the resilient member, or base member, containing the resilient filaments engages tissue at an incision site, the tips of some of the filaments, again based on the angle of orientation of these filaments in relation to the tissue being retracted, will abut against the tissue and impart a resistive force against the tissue along the direction of the filament. In one embodiment of the invention, the filaments can be oriented to resist movement of the retracted tissue relative to the base member in a lateral direction along the sides of the incision and in an upwardly direction away from the patient's body.

It is a further object of the present invention to provide attachable pads or members for a surgical clamp or other occlusion device, or a surgical retractor, that contain gripping surfaces and arrays of filaments extending at acute angles relative to the surfaces for engagement with vessels or tissue. Again, these filaments are such that when the particular device is engaged with a vessel or other tissue, the filaments abut against the vessel or tissue to resist and restrict movement of the vessel or tissue in a direction opposed to the orientation of the filaments.

BRIEF DESCRIPTION OF THE DRAWINGS

FIG. 16 is a perspective view of a surgical clamp pad according to the present invention with resilient filaments extending from along the sides of the pad;

FIG. 17 is a side view of the FIG. 16 pad;

FIG. 18A is a cross-sectional view of the pad shown in FIG. 17 taken along line 18A—18A of FIG. 17;

FIGS. 18B–18D are cross-sectional views of pads according to the present invention showing different configurations of resilient filaments;

FIG. 24 is an exploded perspective view illustrating resilient filaments according to the present invention secured along individual spines;

FIG. 25 is a perspective view illustrating the resilient filaments and spines of FIG. 24 in an assembled nested condition;

FIG. 26 is a perspective view illustrating the assembled resilient filaments and spines of FIG. 25 embedded in a resilient cushion;

FIGS. 32A–32E are side views illustrating different configurations of resilient filaments which may be used in the present invention;

FIGS. 33A–33E are end views of the resilient filaments of FIGS. 32A–32E, respectively.

DETAILED DESCRIPTION OF THE INVENTION

Figure 1:
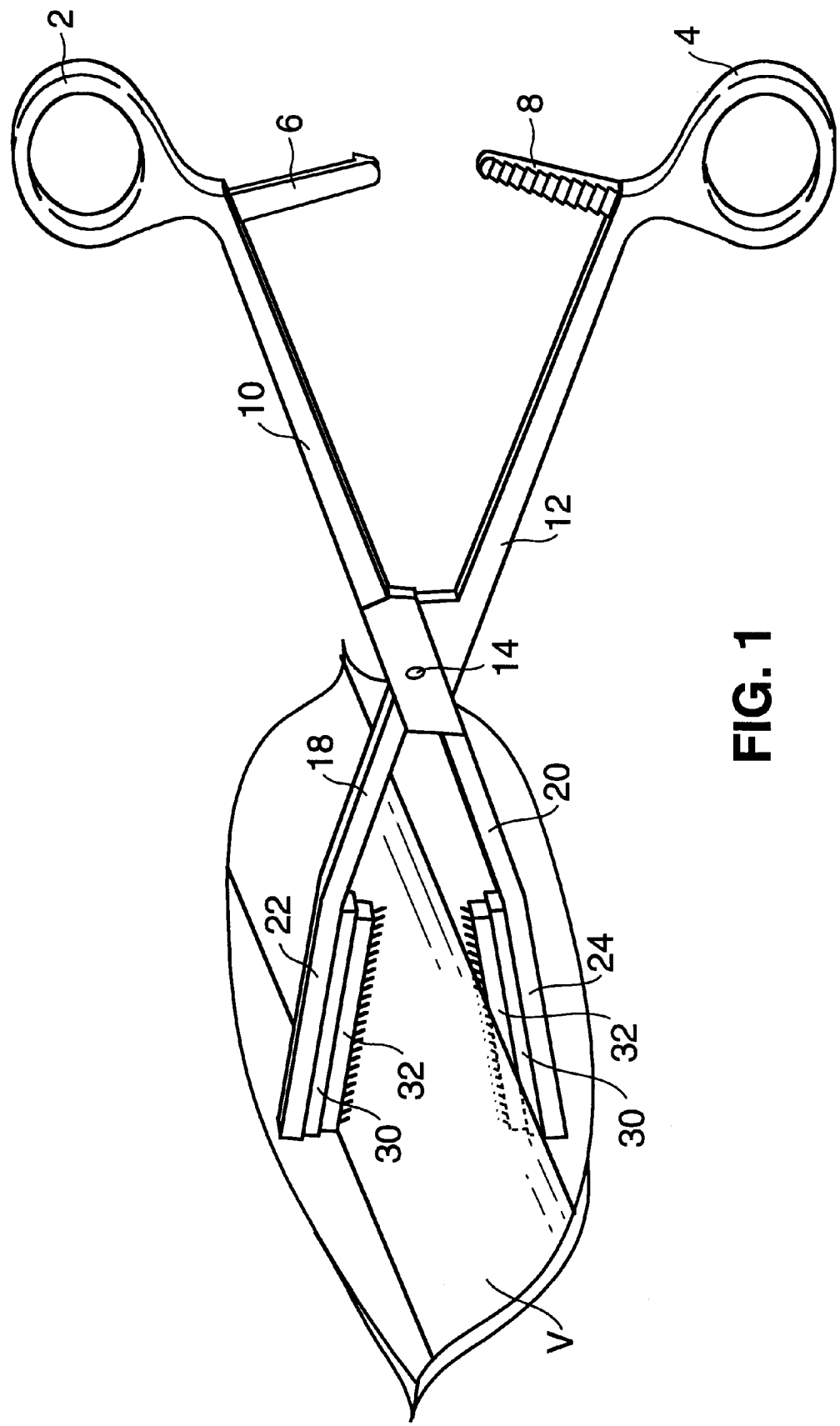
FIG. 1 is a perspective view of a surgical clamp according to the present invention in a position to engage a vessel.

FIG. 1 is a surgical clamp comprising a pair of opposed jaws 22 and 24 and handles 10 and 12 hinged together by pin 14. The handles 10 and 12 terminate in finger and thumb rings 2 and 4 which provide for manual operation of the jaws by a surgeon. Interlocking pawl 6 and ratchet teeth 8 are provided on handles 10 and 12, respectively, to secure jaws 22 and 24 in an adjusted clamped position with a vessel V. In FIG. 1, opposed jaws 22 and 24 are positioned to engage vessel V. The opposed jaws 22 and 24 include opposed pads 32, 32 attached to members 30, 30 which are in turn detachably secured to opposed jaws 22 and 24.

Figure 2:
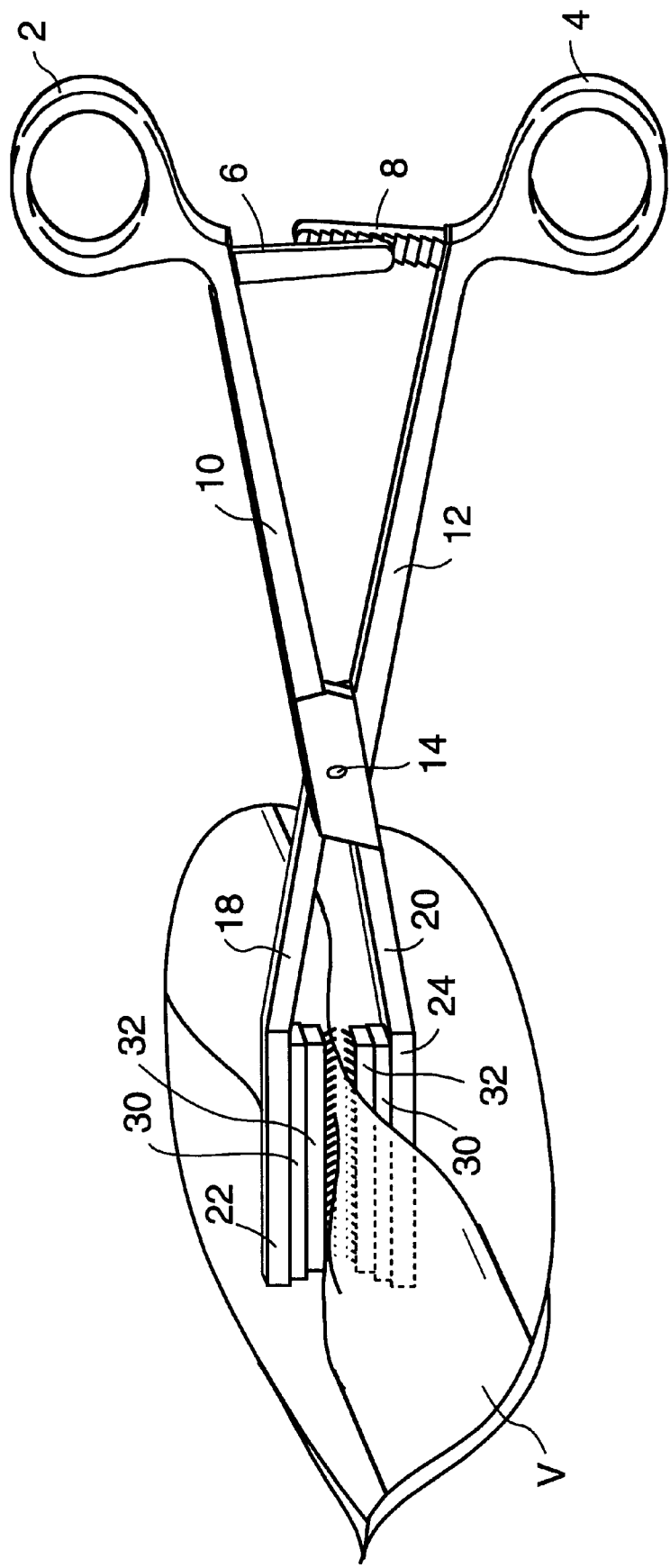
FIG. 2 is a perspective view of the surgical clamp of FIG. 1 engaged with and occluding a vessel.

FIG. 2 shows the surgical clamp with opposed jaws 22 and 24 in an adjusted clamped position. The opposed pads 32, 32 clamp vessel V, thereby causing occlusion of vessel V. Interlocking ratchet teeth 8 are engaged with interlocking pawl 6 to secure the opposed jaws in the clamped position.

Figures 3, 4:
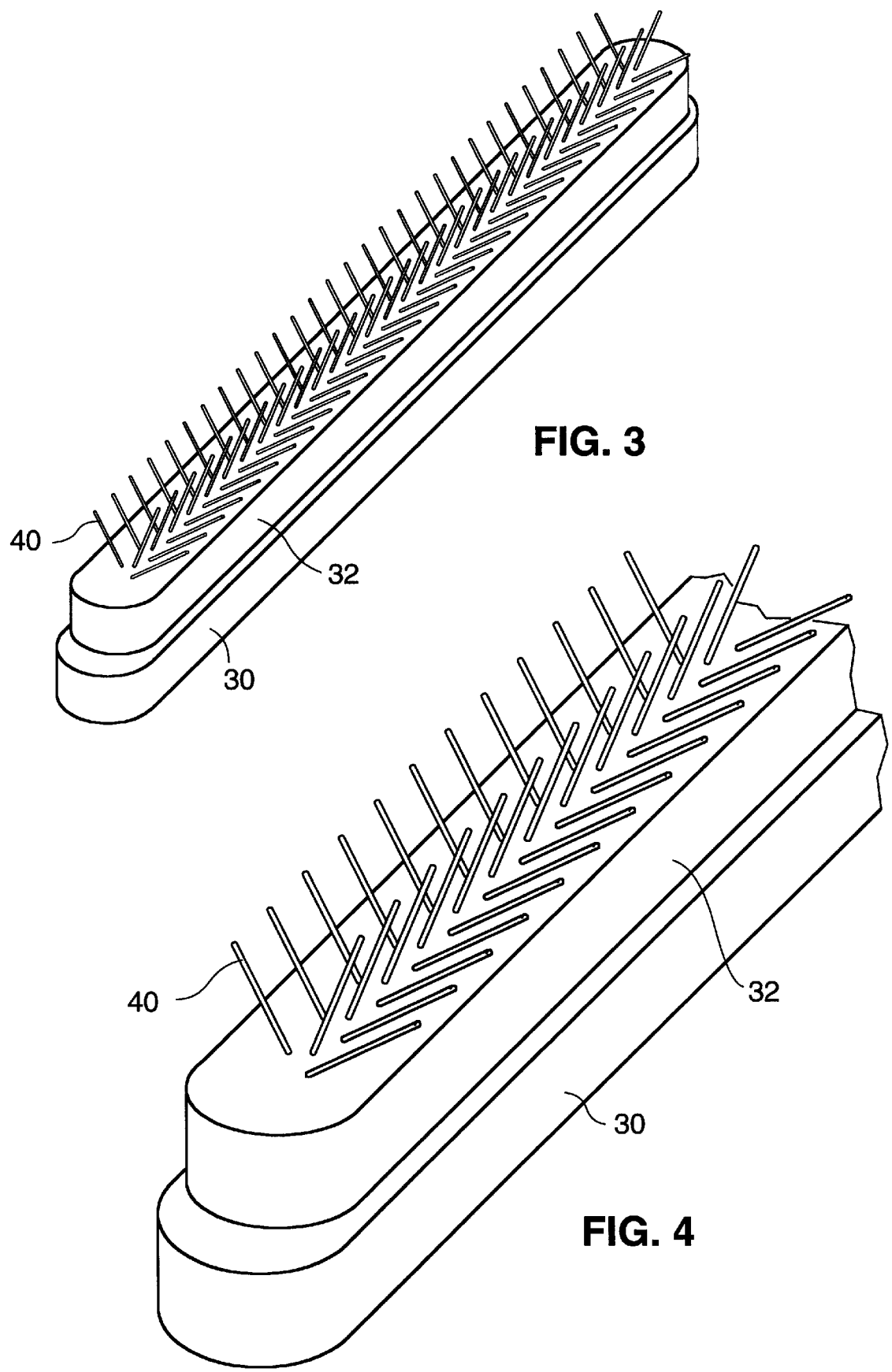
FIG. 3 is a perspective view of a surgical clamp pad capable of attachment to the jaw of a surgical clamp, with a surface containing resilient filaments according to the present invention.
FIG. 4 is an enlarged perspective view of the surgical clamp pad of FIG. 3, with parts broken away.

An embodiment of the pad 32 and attaching member 30, is depicted in FIGS. 3 and 4. The pad 32 includes resilient filaments 40 for resisting movement of an occluded vessel relative to the pad 32. As FIGS. 3 and 4 depict, the resilient filaments 40 extend from the pad 32 at acute angles relative to the surface of the pad 32. Any acute angle relative to the surface will operate to resist relative movement of an occluded vessel. The preferred angle is 45 degrees relative to the surface.

The resilient filaments 40 are comprised of a durable yet flexible material, such as nylon or polyester. The filaments cannot be so rigid that they puncture the occluded vessel, but they must be of a strength and resiliency such that they resist a force in a direction opposed to the orientation of the filaments. The effective length of the filaments will depend on the length to diameter ratio of the filaments. Filaments that are too short and wide and too rigid may puncture the vessel, whereas filaments too long and narrow may fold over upon themselves when a force is applied and will be unable to restrict relative movement of the vessel. The preferred length of the filaments is 0.030 to 0.075 inches, most preferably 0.060 inches. The preferred diameter of the filaments is 0.005 to 0.012 inches, preferably 0.007 inches. Wider filaments may be used, provided they are sufficiently flexible. The ends or tips of the filaments themselves can comprise a variety of shapes, as depicted in FIGS. 24 and 25. For example, filament 101 has a rounded tip, filament 102 has an angled-cut tip, filament 103 has a blunt-cut tip, filament 104 has a pointed tip, and filament 105 has a semi-rounded tip. Also, the filaments can be cylindrical 101–103, semi-cylindrical 105, or contain three sides 104 or more. The preferred filament is cylindrical with a rounded tip, as exemplified by filament 101. The pad 32 is itself comprised of a resilient material, preferably silicone. The most preferred composition of the pad 32 is two part silicone of less than a 20 durometer, liquid injection moldable (GE 6040) or a silicone foam such as GE RTF762.

Figure 5:
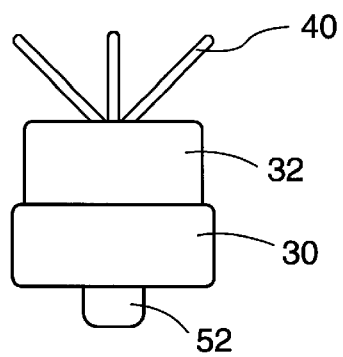
FIG. 5 is an end view of the surgical clamp pad of FIG. 3.
Figure 6:
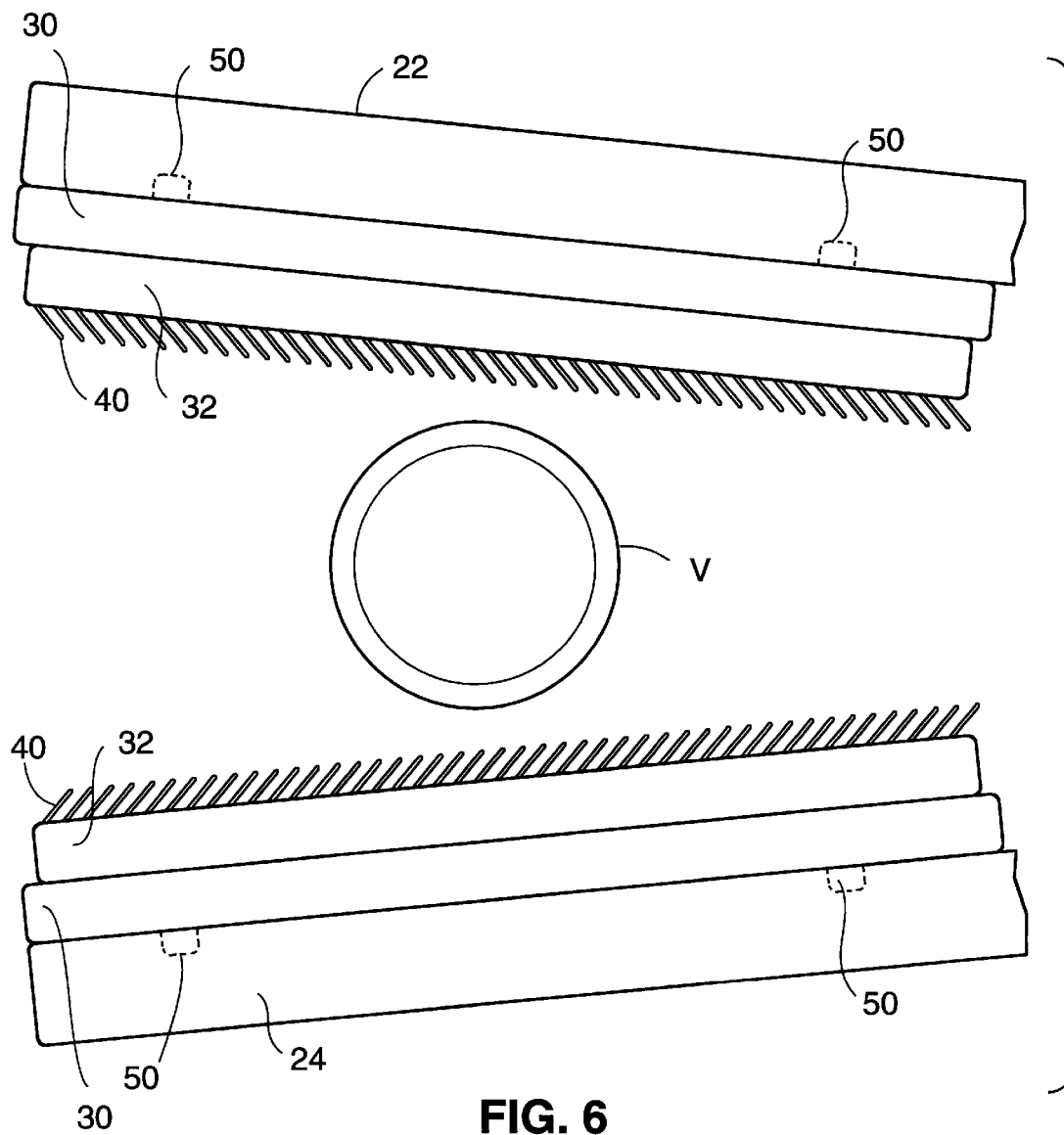
FIG. 6 is a side view of opposed jaws of a surgical clamp with attached clamp pads of FIG. 3 which include opposed surfaces containing resilient filaments, positioned to engage a vessel.

Member 30 provides a rigid backing for pad 32 and means for attachment of pad 32 to opposed jaws 22 and 24. As depicted in FIGS. 5 and 6, a means for attaching pad 32 to an opposed jaw 22 or 24 can comprise a pair of protrusions 52 on member 30 detachably coupled to recesses 50 on the jaw.

Figure 7:
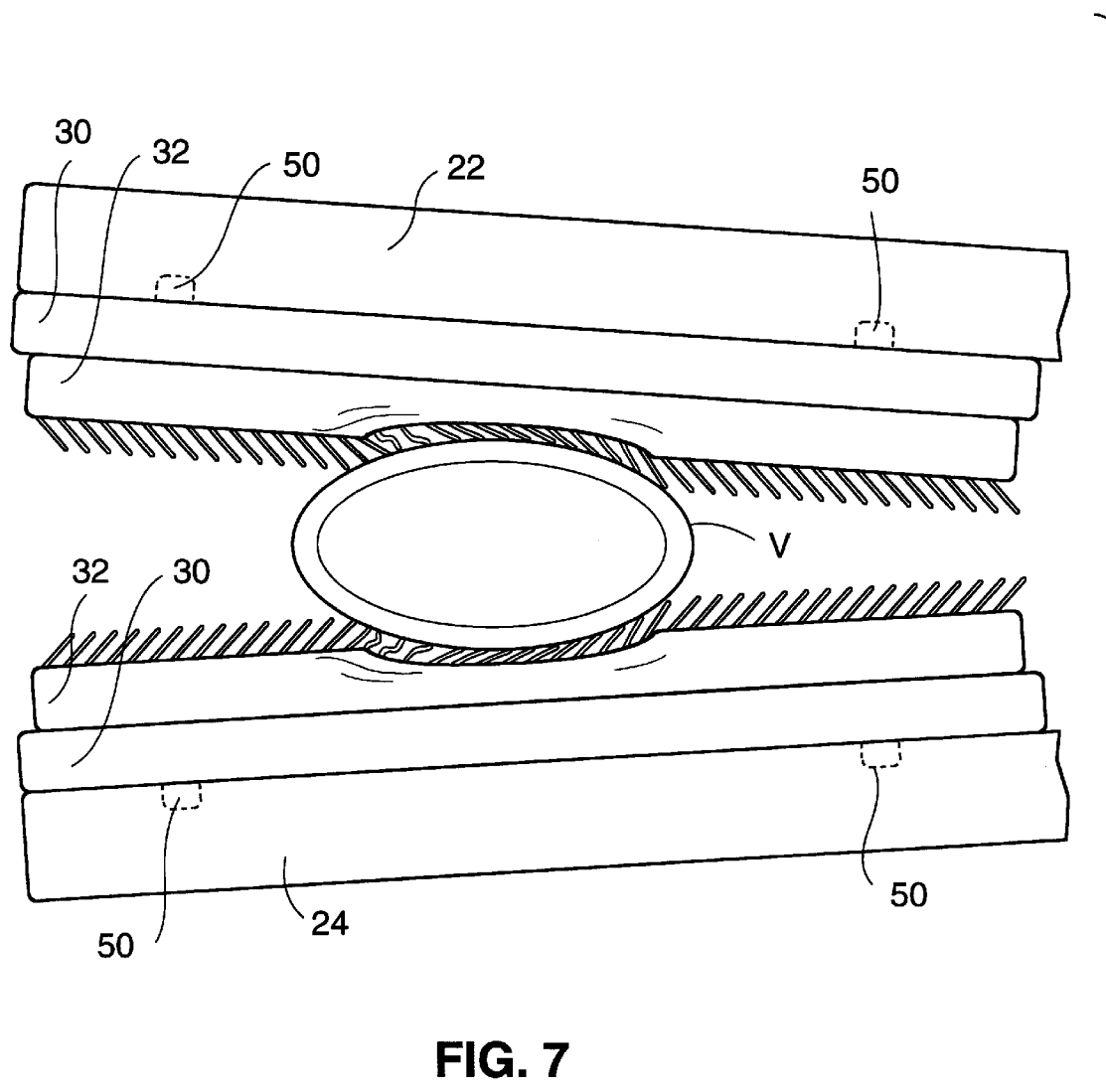
FIG. 7 is a side view according to FIG. 6 where the opposed surfaces containing resilient filaments have engaged the vessel, and the vessel is partially occluded.
Figure 8:
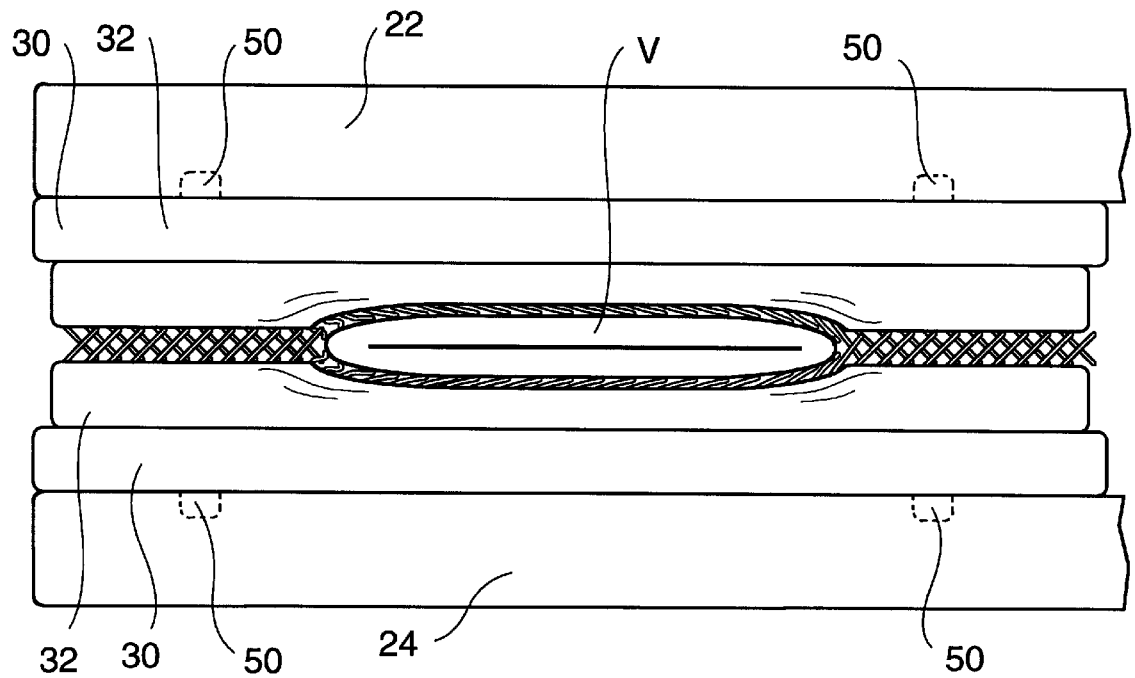
FIG. 8 is a side view according to FIG. 7 where the opposed surfaces containing resilient filaments have fully engaged the vessel and the vessel is occluded.

The operation of one embodiment of the invention is depicted in FIGS. 6, 7 and 8. FIG. 6 illustrates upper and lower jaws 22 and 24, opposed members 30, 30, and opposed pads 32, 32 with resilient filaments 40 in a position to engage and occlude vessel V. FIG. 7 illustrates the above components in partial engagement with vessel V. As depicted in FIG. 7, the resilient members 32, 32 have deflected to accommodate the shape of vessel V, thereby minimizing trauma to vessel V. FIG. 8 shows the above components in complete engagement with vessel V causing occlusion of vessel V. Some of the resilient filaments have been pressed flat along the resilient members 32, 32 due to the angle at which the vessel V engages those filaments. Other resilient filaments remain generally oriented along an acute angle relative to the pads 32, 32 and abut vessel V. The abutment of some of the resilient filaments against the vessel V creates a resistive force against movement of the vessel V in a direction opposed to the orientation of the abutting filament or filaments. This resistive force assists in securing vessel V against movement relative to pads 32, 32 and opposed jaws 22 and 24.

Figure 9A:
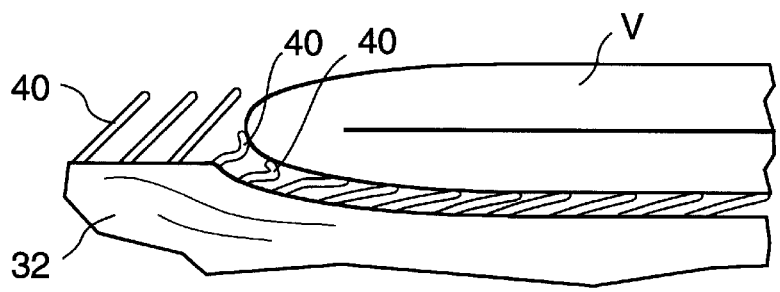
FIG. 9A is an enlarged side view of FIG. 8 showing the resilient filaments of the lower opposed surface engaged with the vessel in greater detail.

In the embodiment illustrated in FIGS. 8 and 9A, the resilient filaments 40 are oriented such that the filaments on the lower pad 32 that abut vessel V will impart a resistive force upward, thereby pushing or levering the vessel V upward into the upper pad 32 in a direction along the general direction of orientation of resilient filaments. The resilient filaments on the upper pad 32 that abut the vessel V will impart a downward resistive force along the general direction of orientation of those particular resilient filaments. In combination, the embodiment as shown in FIG. 8 will resist movement of the occluded vessel V in one lateral direction relative to the opposed jaws 22 and 24 while permitting lateral movement of the occluded vessel V in the opposite lateral direction relative to the opposed jaws 22 and 24. In the preferred embodiment, lateral movement of the occluded vessel V will be restricted toward the distal ends of the opposed jaws 22 and 24.

Figure 9B:
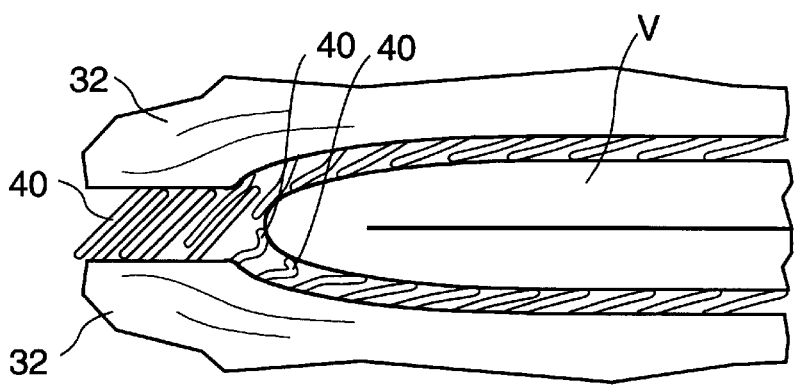
FIG. 9B is an enlarged side view similar to FIG. 9A showing the resilient filaments of the upper opposed surface in a different orientation.

In another embodiment, as depicted in FIG. 9B, the orientation of the resilient filaments of the upper opposed pad 32 can be reversed from that of FIG. 8 such that the resistive force resulting from the filaments on one jaw abutting the vessel restricts lateral movement of the vessel V in one lateral direction relative to opposed pads 32, 32, while the resistive force resulting from the filaments on the other jaw abutting the vessel restricts lateral movement of the vessel V in the opposite lateral direction relative to opposed pads 32, 32.

Figure 10:
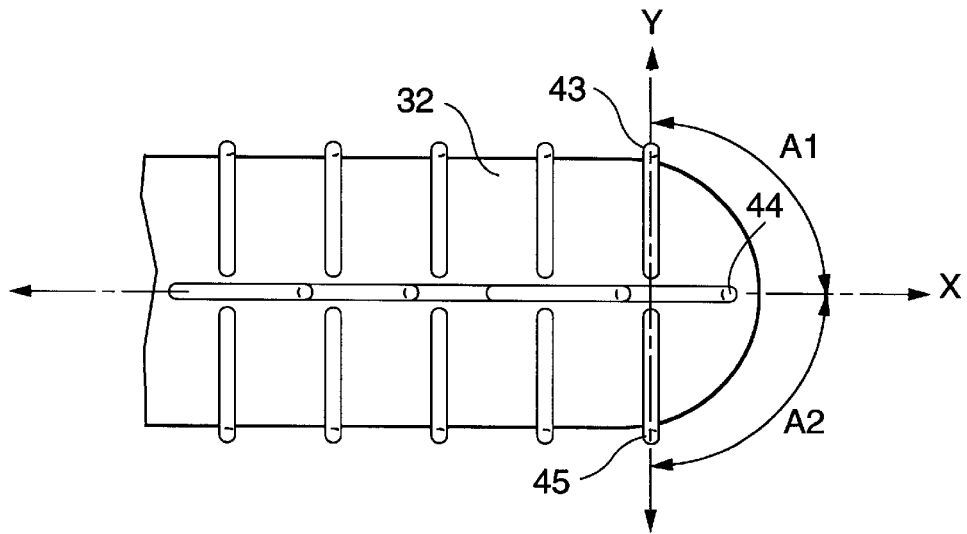
FIG. 10 is a top view of a pad constructed according to the present invention having a different arrangement of resilient filaments, with part of the pad broken away.
Figure 11:
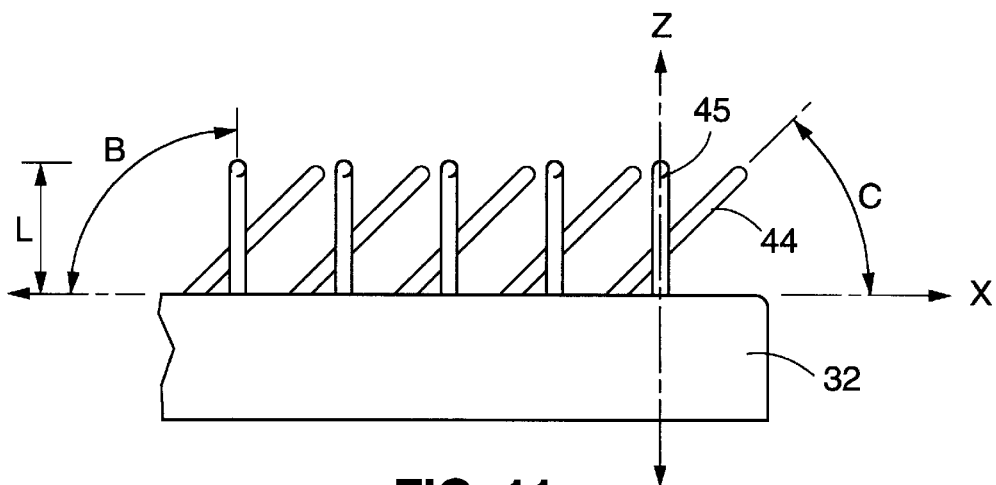
FIG. 11 is a side view of the FIG. 10 pad.
Figure 12:
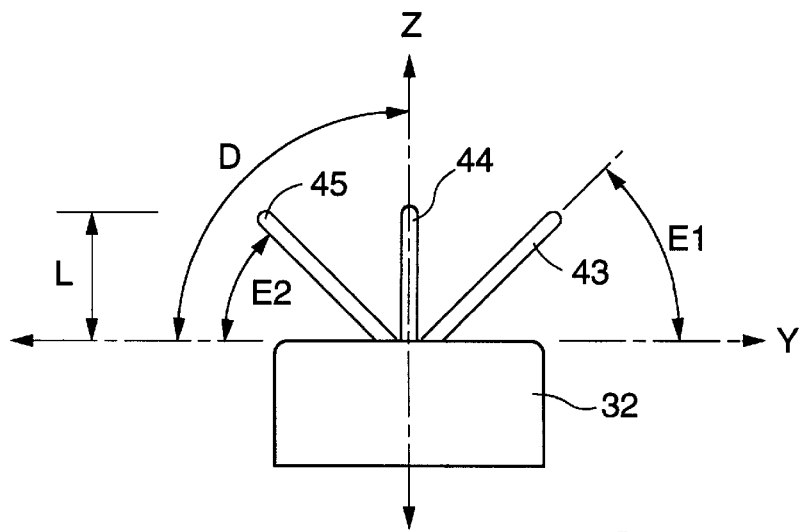
FIG. 12 is an end view of the FIG. 10 pad.

The resilient filaments can be arranged in one or more rows, and oriented in one or more directions. FIGS. 10–12 depict an embodiment of a particular arrangement of resilient filaments 43–45 extending from the pad 32 arranged in three distinct rows and oriented in three separate directions. The surface of pad 32 defines a plane (surface plane) containing two axes, an axis X running the length of the pad (longitudinal axis), and an axis Y oriented perpendicular to axis X (perpendicular axis). A third axis Z intersects the plane in an orientation normal to the plane (normal axis). In this embodiment, one row of resilient filaments, comprised of resilient filaments 44, is arranged in a row along longitudinal axis X, and the filaments of this row are oriented at an acute angle C from the surface of the pad 32 in a plane defined by longitudinal axis X and normal axis Z, and at an angle D from the surface in a plane defined by perpendicular axis Y and normal axis Z. A second row of resilient filaments, comprised of filaments 43, is arranged along an axis parallel to longitudinal axis X, and the filaments of this row are oriented at an angle A1 from longitudinal axis X in the surface plane, at an angle B from the surface of the pad 32 in a plane defined by longitudinal axis X and normal axis Z, and at an acute angle E1 from the surface in a plane defined by perpendicular axis Y and normal axis Z. A third set of resilient filaments, comprised of filaments 45, is likewise arranged along an axis parallel to longitudinal axis X, and the filaments of this row are oriented at an angle A2 from longitudinal axis X in the surface plane, and in a direction generally opposed to the direction of the filaments of the second row with respect to this plane, at an angle B from the surface of the pad 32 in a plane defined by longitudinal axis X and normal axis Z, and at an acute angle E2 from the surface in a plane defined by perpendicular axis Y and normal axis Z. This arrangement of resilient filaments, when engaged with a vessel, will resist movement of the vessel relative to the pad 32 in either direction along perpendicular axis Y, and will also resist movement of the vessel relative to the pad 32 in one of two directions along longitudinal axis X.

In the preferred embodiment, the angles A1, A2, B and D are approximately 90 degrees while the angles C, E1 and E2 are between 30 to 60 degrees, most preferably approximately 45 degrees. The number of resilient filaments per row can be between 8 and 32, and is preferably 16. Also, it is preferable, though not necessary, that the filaments terminate at the same height L relative to the surface of the pad 32.

Figure 13:
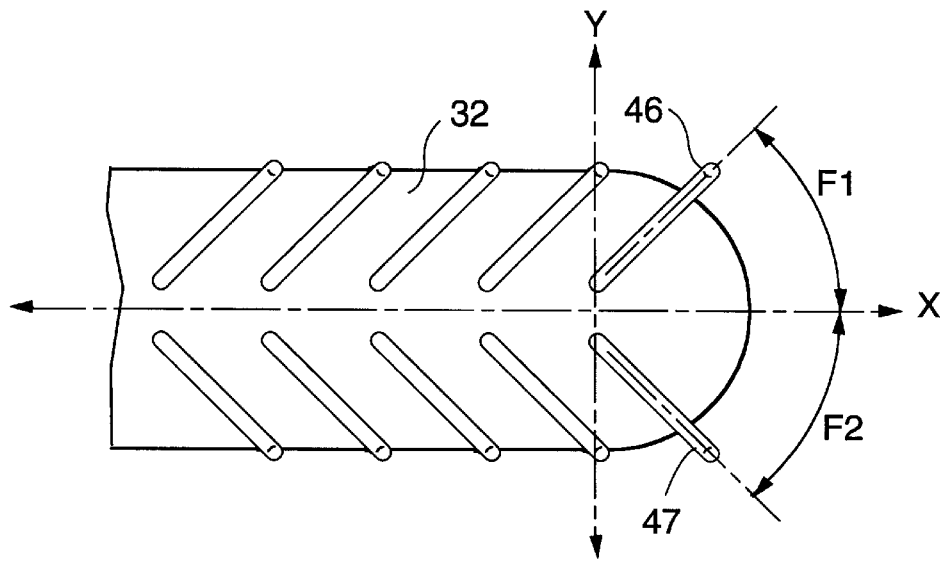
FIG. 13 is top view similar to FIG. 10 of a pad constructed according to the present invention having yet another arrangement of resilient filaments, with part of the pad broken away.
Figure 14:
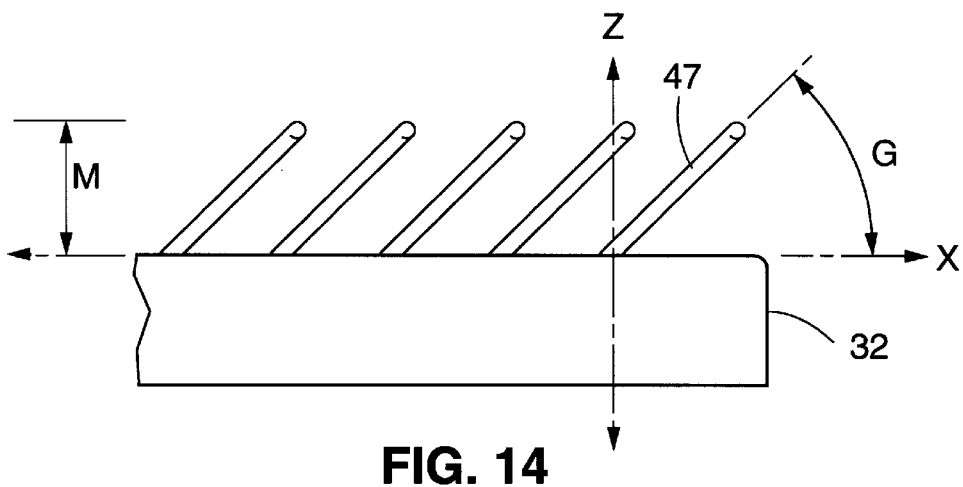
FIG. 14 is a side view of the FIG. 13 pad.
Figure 15:
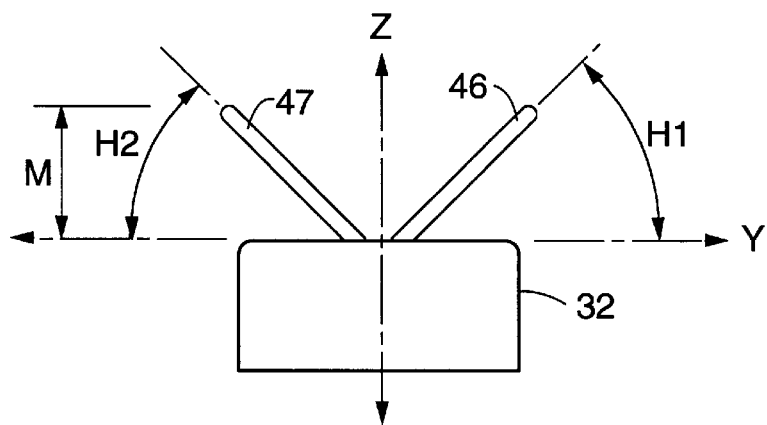
FIG. 15 is an end view of the FIG. 13 pad.

An alternative arrangement of filaments is depicted in FIGS. 13–15. In this embodiment, resilient filaments extending from pad 32 (having a surface plane and longitudinal, perpendicular, and normal axes, X, Y and Z, as described above for FIGS. 10–12) are arranged in two distinct rows and are oriented in two separate directions. A first row of resilient filaments, comprised of resilient filaments 46, is arranged along an axis parallel to longitudinal axis X, and the filaments of this row are oriented at an acute angle F1 from longitudinal axis X in the surface plane, at an acute angle G from the surface of pad 32 in a plane defined by longitudinal axis X and normal axis Z, and at an acute angle H1 from the surface in a plane defined by perpendicular axis Y and normal axis Z. A second row of resilient filaments, comprised of resilient filaments 47, is likewise arranged along an axis parallel to longitudinal axis X, and the filaments of this row are oriented at an acute angle F2 from longitudinal axis X in the surface plane, at an acute angle G from the surface of the pad 32 in a plane defined by longitudinal axis X and normal axis Z, and at an acute angle H2 from the surface in a plane defined by perpendicular axis Y and normal axis Z. The sum of acute angles F1 and F2 is less than 180 degrees. This arrangement of resilient filaments, when engaged with a vessel, will resist movement of the vessel relative to the pad 32 in either direction along perpendicular axis Y, and will also resist movement of the vessel relative to the pad 32 in one of two directions along longitudinal axis X.

In the preferred embodiment, the angles F1, F2, G, H1 and H2 are between 30 to 60 degrees, most preferably approximately 45 degrees. The number of resilient filaments per row can be between 12 and 48, and is preferably 24. Also, it is preferable, though not necessary, that the filaments terminate at the same height M relative to the pad 32.

Another embodiment of the pad 32 and attaching member 30 is depicted in FIG. 16. In this embodiment, resilient filaments 40 extend outward from a position where pad 32 attaches to member 30, at an acute angle relative to the surface of pad 32. Any acute angle relative to the surface will operate to resist relative movement of an occluded vessel, the preferred angle being 45 degrees.

FIGS. 16–18A depict an embodiment of a particular arrangement of resilient filaments extending from between pad 32 and member 30 in two sets, one on each side of pad 32. Each set of filaments is organized into two intersecting groups. The filaments of both groups extend from between pad 32 and member 30 along a single plane. The filaments of each group are oriented parallel to one another and at an angle relative to the filaments of the other group. The preferred angle is a right angle. The planes defined by each set of filaments are oriented at an angle L relative to the surface of pad 32. The preferred angle L is between 45 to 90 degrees, and is most preferably 45 degrees. This arrangement of filaments, when engaged with a vessel, will resist movement of the vessel in either direction relative to the length of the pad. When angle L is less than 90 degrees, the arrangement will also resist movement of an engaged vessel in a direction transverse to the length of the pad.

As depicted in FIG. 18A, the distal ends of the filaments terminate at a position above the surface of pad 32. In an alternative embodiment depicted in FIG. 18C, the filaments terminate at a position below the surface of pad 32. In the preferred embodiment, the filaments terminate at a position sightly above the surface of pad 32. It is also preferable, although not necessary that the filaments terminate at the same height relative to the surface of pad 32.

In the embodiment depicted in FIG. 18A, the filaments 40 are mounted between pad 32 and member 30 and extend outwardly on each side of pad 32. In the preferred embodiment there shown, member 30 has a channel with angled sides that accommodate the filaments 40. The pad 32 has a bottom surface with a reciprocal shape to fit the channel of member 30. In alternative embodiments depicted in FIGS. 18B and 18C, member 30 has a channel with perpendicular sides. In these embodiments, pad 32 has a flat bottom surface and the filaments 40 are again accommodated between the bottom surface of pad 32 and the channel of member 30. In another alternative embodiment, as depicted in FIG. 18D, the pad is divided into upper and lower portions 32a and 32b, and filaments 40 are mounted between the portions and extend outwardly on each side of the pad. The lower portion 32b preferably has a channel with angled sides for receiving the filaments 40 and the upper portion 32a, which has a reciprocally-shaped bottom surface, as depicted in FIG. 18D.

Figure 19:
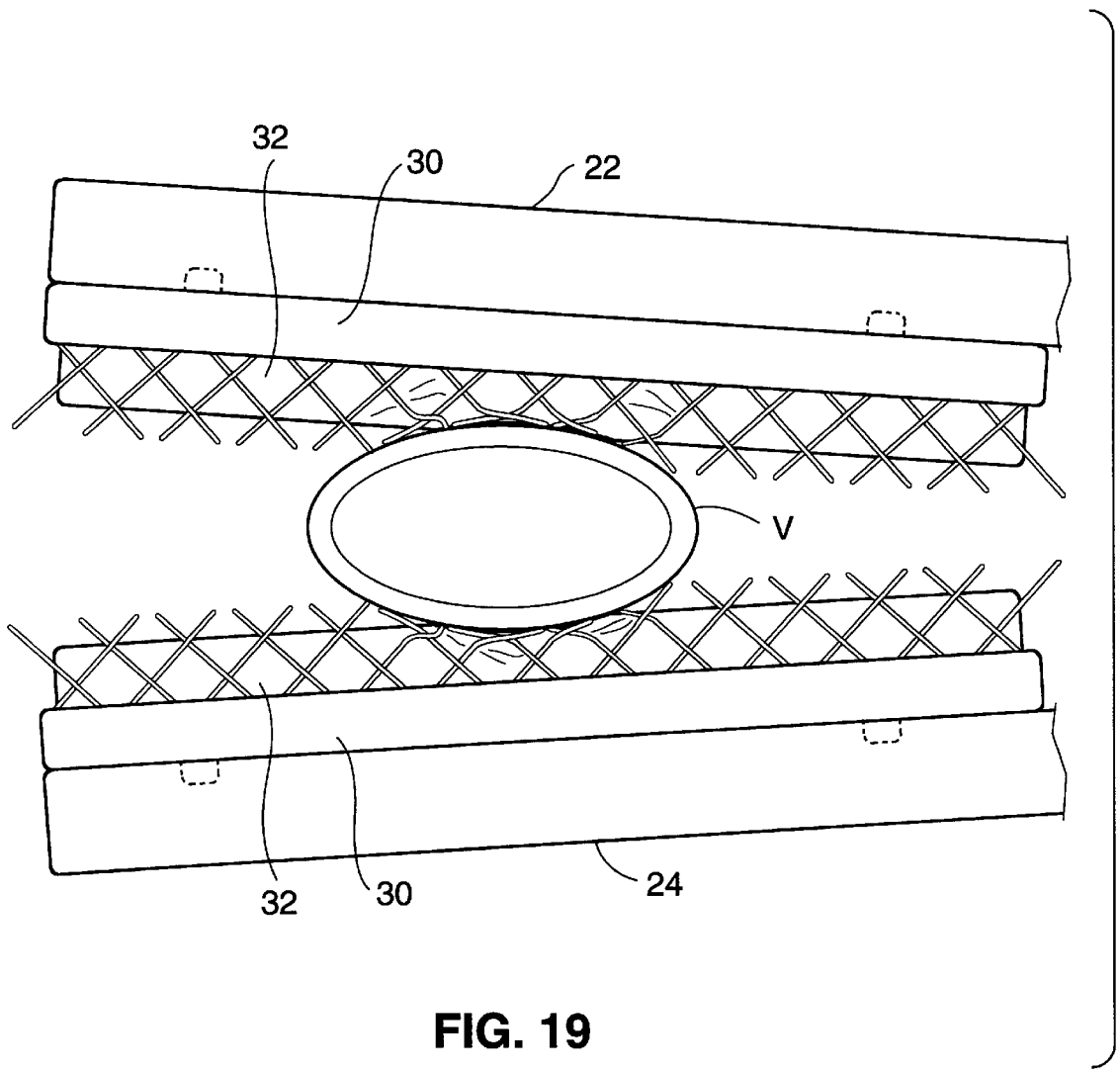
FIG. 19 is a side view of opposed jaws of a surgical clamp with attached clamp pads of FIG. 16 which include opposed surfaces and resilient filaments, and where the surfaces and filaments have engaged the vessel and the vessel is partially occluded.

The operation of the embodiment of the invention depicted in FIGS. 16–18 is illustrated in FIG. 19. FIG. 19 illustrates upper and lower jaws 22 and 24, and opposed members 30, 30 and opposed pads 32, 32 having resilient members mounted therebetween, in partial engagement with vessel V. The filaments have engaged the vessel V, as have the resilient surfaces of pads 32, 32 which have deflected to accommodate the vessel in atraumatic fashion. The abutment of some of the filaments against the vessel V creates a resistive force against movement of the vessel. In the alternative embodiment where the distal tips terminate below the surface of the pads, the pads engage vessel V first and deflect until the filaments also engage the vessel V.

Figure 20:
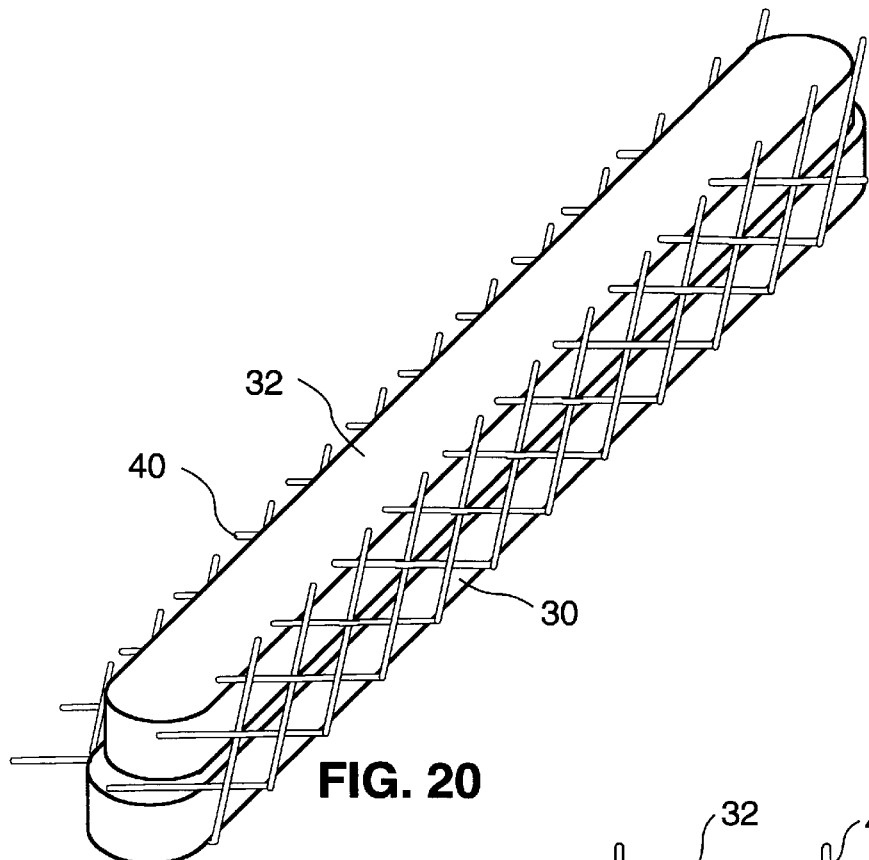
FIG. 20 is a perspective view of a surgical clamp pad with resilient filaments according to the present invention.
Figure 22:
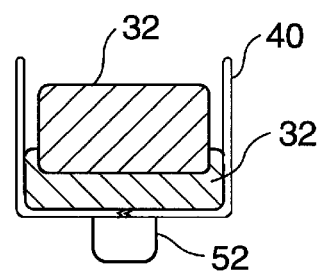
FIG. 22 is a cross-sectional view of the pad shown in FIG. 21 taken along line 22—22 of FIG. 21.
Figure 21:
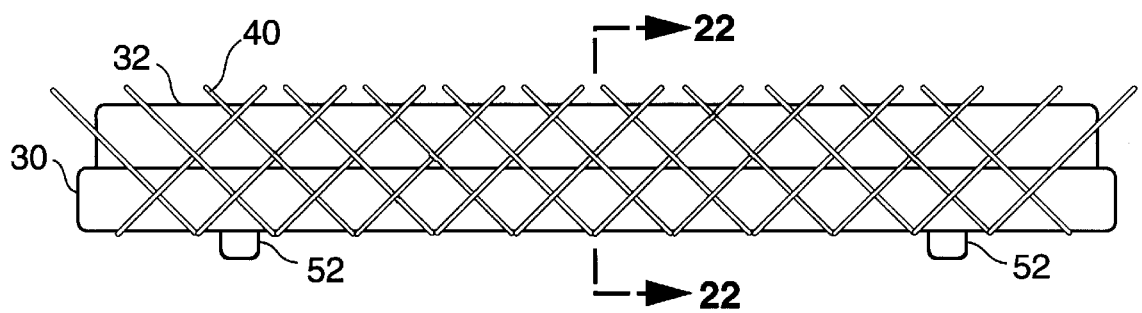
FIG. 21 is a side view of the FIG. 20 pad.
Figure 23:
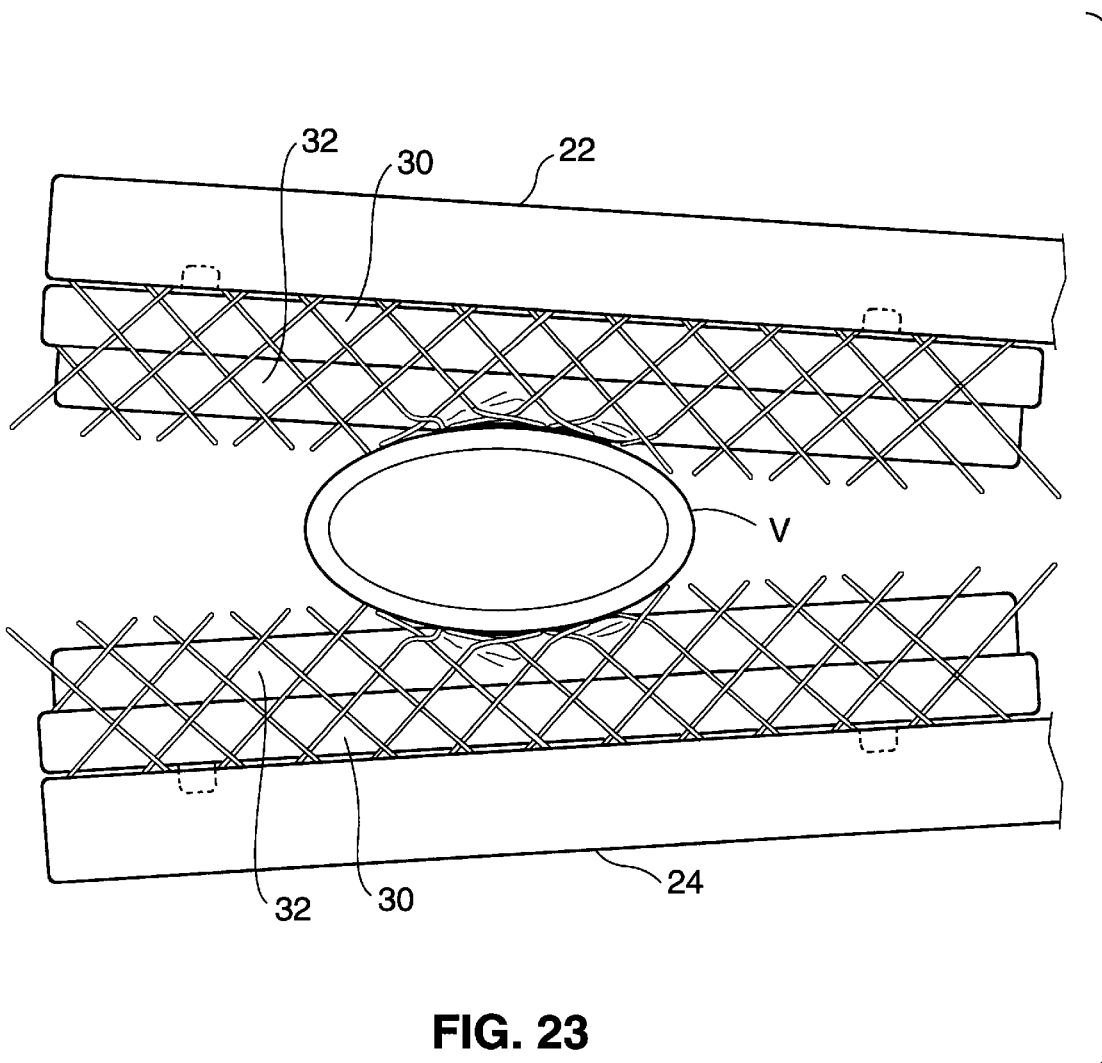
FIG. 23 is a side view of opposed jaws of a surgical clamp with attached clamp pads of FIG. 20 which include opposed surfaces and resilient filaments, and where the surfaces and filaments have engaged the vessel and the vessel is partially occluded.

An alternative arrangement of filaments is depicted in FIGS. 20–22. In this embodiment, the filaments 40 are arranged in similar fashion to the embodiment depicted in FIG. 16. Two sets of filaments 40 extend from each side of the pad 32 and each set of filaments is organized into two groups oriented in a single plane with the filaments in each group oriented parallel to one another and at an angle to relative to the filaments of the other group, the preferred angle being a right angle. The filaments themselves, however, are mounted, and extend from, the base member 30 itself, as depicted in FIGS. 20–22. In the preferred embodiment, the distal tips of the filaments terminate at a position above the surface of pad 32. In alternative embodiments, the tips terminate at a position even with or below the surface of the pad (see, e.g., FIG. 18C). The operation of this embodiment of the invention is depicted in FIG. 23 and is essentially identical in operation to that of the embodiment described above and depicted in FIGS. 16–19.

The manufacture of resilient filaments and pads according to the invention can be accomplished in many ways, as will be apparent to one skilled in the art. One method of manufacture is illustrated in FIGS. 24–26. As shown therein, filaments are secured in particular orientations along spines 60, 62 and 64. These spines are arranged in interlocking fashion, as shown in FIG. 25, and then embedded into pad 32, as depicted in FIG. 26. In the preferred method, the arranged spines 60, 62 and 64 are secured in a mold, which is then filled with liquid injection moldable silicone or silicone foam, and the silicone is allowed to cure to form a pad 32 around the filaments.

The embodiments of the invention described above and depicted in FIGS. 16–23 can be manufactured using a plastic weave, such as a nylon mesh or a polyester braid. The plastic weave is comprised of filaments useful in the present invention. A cylindrical sleeve of the weave is cut in half and one portion is heat treated in a mold to shape the weave into a form that will fit into the channel portion of member 30 as described above and depicted in FIGS. 18A–18C. The treated portion of the weave is then secured in the channel portion of member 30, preferably using an adhesive, together with pad 32. As described above, the pad itself is comprised of resilient material, preferably liquid injection moldable silicone or silicone foam. In an alternative manufacturing method, the pad 32 is placed within a cylindrical sleeve of the weave and both are bonded to member 30. The weave is then cut along its axis at or near the surface of pad 32.

Figure 27:
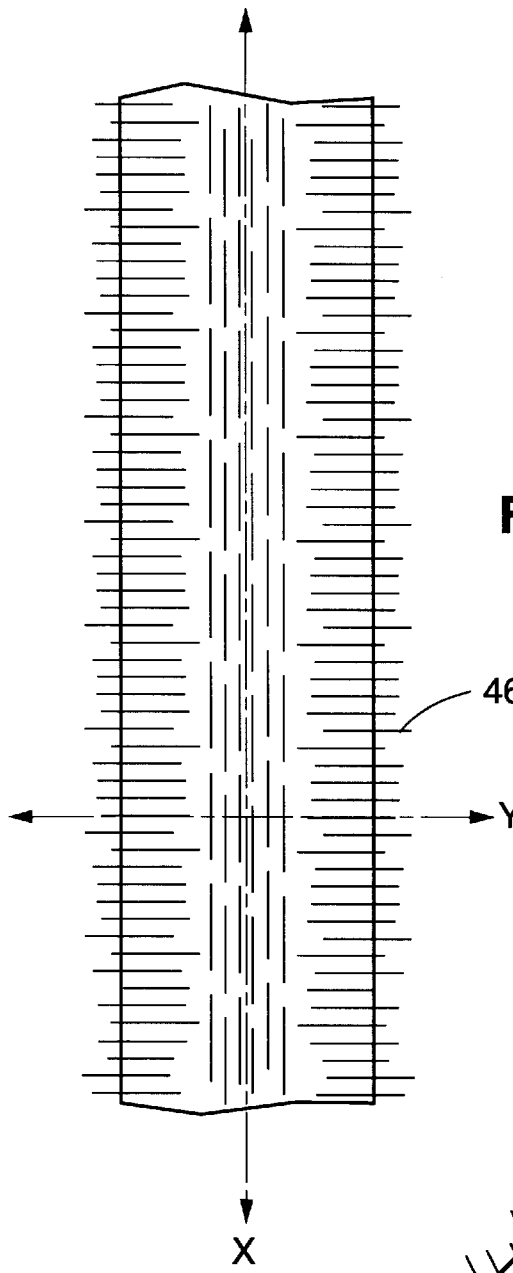
FIG. 27 is a top view of a pad constructed according to the present invention having yet another arrangement of resilient filaments, with parts of the pad broken away.
Figure 28:
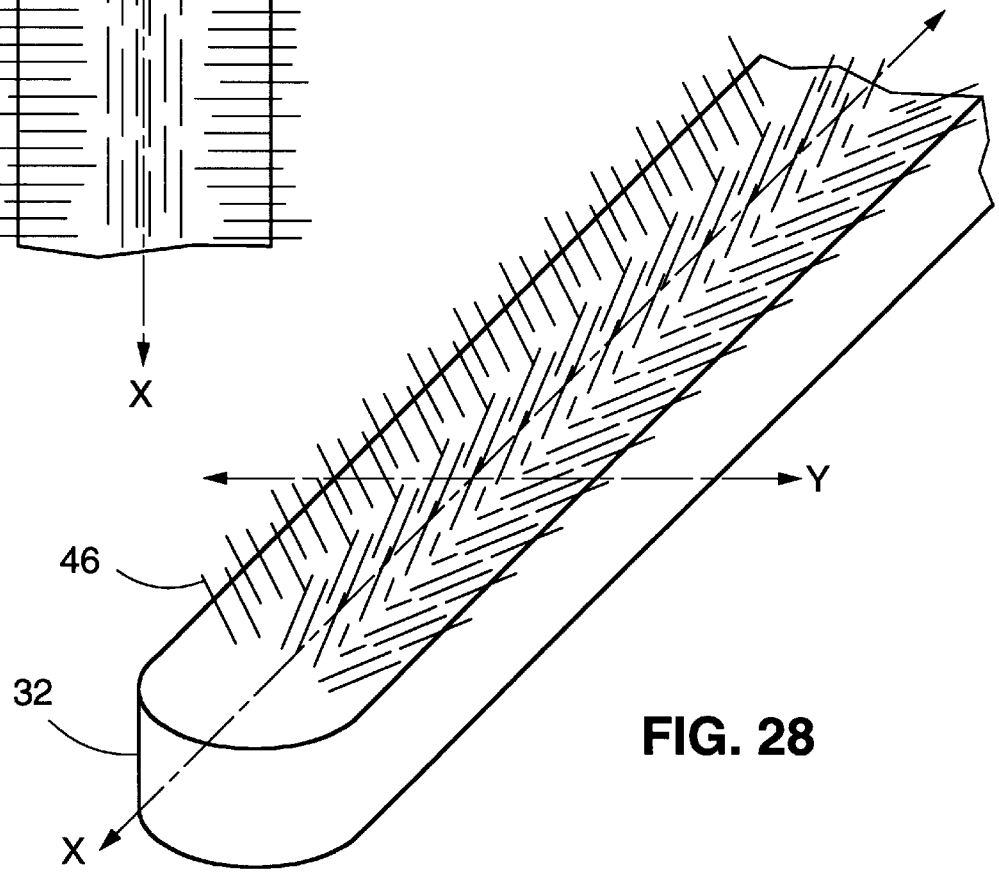
FIG. 28 is a perspective view of the pad shown in FIG. 29.

An alternative embodiment to the above embodiments containing two or three rows of resilient filaments is depicted in FIGS. 27 and 28. In this embodiment, three distinct regions, or strips, of multiple rows of fibers 46 extend from pad 32 (having longitudinal and perpendicular axes, X and V, as described above for FIG. 10–15). Each region or strip contains fibers which are oriented in the same general direction. The three distinct regions are oriented in similar fashion to the three rows of resilient filaments depicted in FIGS. 10–12. The fibers can be comprised of, for example, a synthetic fur. The fibers are resilient enough to resist movement of a vessel which abuts against the tips of the fibers. This arrangement of fibers, when engaged with a vessel, will likewise resist movement of the vessel relative to pad 32 in either direction along perpendicular axis Y of pad 32, and will also resist movement of the vessel in one of two directions along longitudinal axis X. The preferred method of making this embodiment of the invention is to glue or otherwise adhere resilient filaments to a suitable backing material, which is then secured to pad 32.

Figure 29:
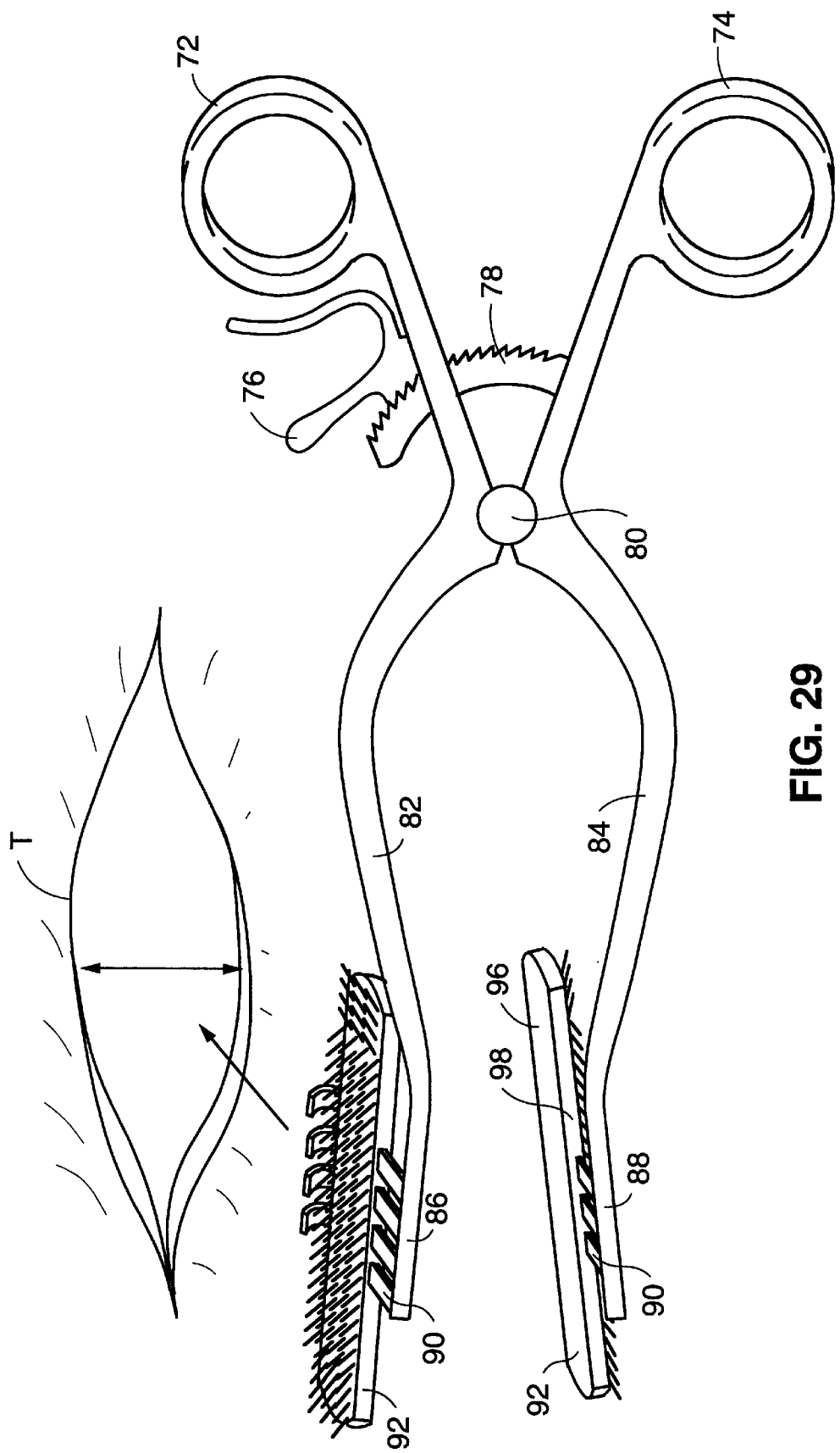
FIG. 29 is a perspective view of a surgical retractor according to the present invention positioned above a surgical incision site.

FIG. 29 is a Weitlaner surgical retractor comprising a pair of opposed retracting arms 82 and 84 hinged together by pin 80. The distal ends of the retracting arms 86 and 88 terminate in retracting fingers 90, 90. The proximal ends of the arms terminate in finger and thumb rings 72 and 74 which provide for manual operation of the retracting arms by a surgeon. The proximal ends of the arms also carry an arcuate rack 78 and locking pawl 76 having interlocking ratchet teeth which engage to secure retracting arms 86 and 88 in an open position when retracting tissue at a surgical incision site.

Figure 30:
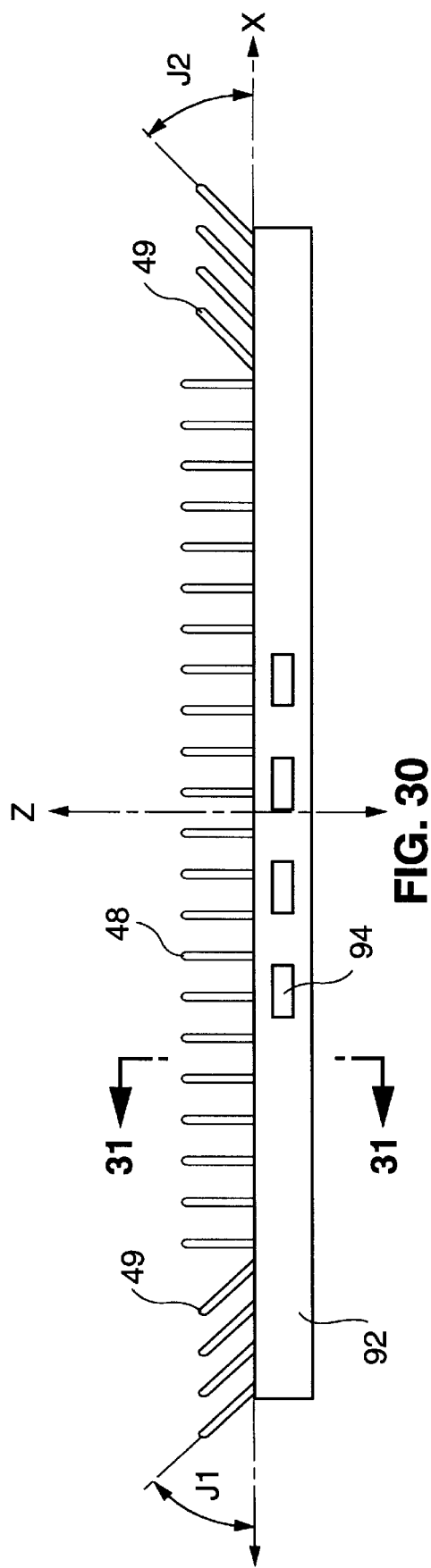
FIG. 30 is a side view of a base member of the surgical retractor shown in FIG. 29.
Figure 31:
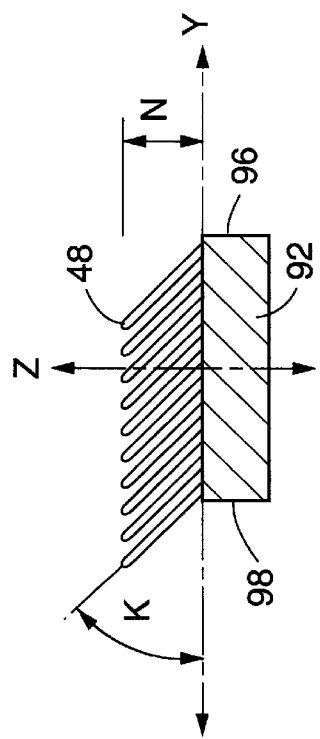
FIG. 31 is a cross-sectional view of the base member shown in FIG. 30, taken on line 31—31 of FIG. 30.

The gripping elements of the retractor comprise base members 92 having resilient filaments which extend from the surface of the base members 92 at acute angles. Each base member 92 is securable to retracting fingers 90. As shown in FIG. 30, base member 92 contains apertures 94 which are adapted to receive retracting fingers 90 formed on the arms 86, 88. As shown in FIG. 31, each base member 92 itself has a distal edge 96 and a proximal edge 98.

As is the case with the surgical clamp discussed above, resilient filaments of base member 92 are comprised of a durable yet flexible material, such as nylon or polyester. The filaments cannot be so rigid that they puncture or otherwise traumatize the retracted tissue, but they must be of a strength and resiliency such that they resist a force in a direction opposed to the orientation of the filaments. The effective length of the filaments will depend on the length to diameter ratio of the filaments. Filaments that are too short and wide may puncture or traumatize the retracted tissue, whereas filaments too long and narrow may fold over upon themselves when a force is applied and will be unable to restrict relative movement of the retracted tissue. The preferred length of the filaments is 0.030 to 0.075 inches, most preferably 0.060 inches. The preferred diameter of the filaments is 0.005 to 0.012 inches, preferably 0.007 inches. Wider filaments can be used, provided they are sufficiently flexible. The ends or tips of the filaments themselves can comprise a variety of shapes, as depicted in FIGS. 32 and 33. For example, filament 101 has a rounded tip, filament 102 has an angled-cut tip, filament 103 has a blunt-cut tip, filament 104 has a pointed tip, and filament 105 has a semi-rounded tip. Also, the filaments can be cylindrical 101–103, semi-cylindrical 105, or contain three sides 104 or more. The preferred filament is cylindrical with a rounded tip, as exemplified by filament 101.

The surface of base member 92 can be of a resilient material, preferably silicone. The most preferred composition of the surface of base member 92 is two part silicone of less than a 20 durometer, liquid injection moldable (GE 6040) or a silicone foam such as GE RTF762.

In the embodiment shown in FIGS. 29–31, some of the resilient filaments, comprised of resilient filaments 48, are oriented to resist movement of retracted tissue T relative to the base member 92 in the direction of distal edge 96. The surface of base member 92 defines a plane containing two axes, an axis X running the length of the base member 92 (longitudinal axis) and an axis Y oriented perpendicular to the axis X (perpendicular axis). A third axis Z intersects the plane in an orientation normal to the plane (normal axis). Resilient filaments 48 are oriented at an acute angle K from the surface of base member 92 in a plane formed by perpendicular axis Y and normal axis Z. Additional resilient filaments, comprised of resilient filaments 49, are oriented at acute angles J1 and J2 from the surface of base member 92 in a plane formed by longitudinal axis X and normal axis Z. This arrangement of resilient filaments, when engaged with retracted tissue, will resist movement of the tissue relative to the surface of base member 92 in either direction along longitudinal axis X, and will also resist movement of the tissue relative to the base member 92 along perpendicular axis Y in the direction towards distal edge 96.

In the preferred embodiment, the angles J1, J2, and K are between 30–60 degrees, most preferably approximately 45 degrees, and the number of rows of resilient filaments is 10. It is preferable, though not necessary, that the filaments terminate at the same height N relative to the surface 92.

Although only certain embodiments have been illustrated and described, those having ordinary skill in the art will understand that the invention is not intended to be limited to the specifics of these embodiments, but rather is defined by the accompanying claims.

We claim:

1. A surgical clamp comprising:
   first and second jaws mounted for movement toward and away from each other, said jaws having opposed surfaces; and, resilient filaments mounted on at least one of the jaws and extending therefrom at an acute angle relative to the opposed surface of at least one of the jaws for engagement with a vessel or other tissue received between the jaws when the jaws are moved toward one another, said filaments terminating in free distal ends for abutment against the vessel or other tissue to resist relative movement between the jaws and the vessel or other tissue.

2. A surgical clamp according to claim 1 wherein said resilient filaments are mounted on the opposed surface of at least one of said jaws.

3. A surgical clamp according to claim 1 wherein said filaments are resiliently deflectable to cushion the vessel or other tissue engaged thereby.

4. A surgical clamp according to claim 1 wherein the filaments are monofilament and generally rectilinear.

5. A surgical clamp according to claim 4 wherein the filaments have a length between 0.030 to 0.075 inches and a diameter between 0.005 to 0.012 inches.

6. A surgical clamp according to claim 4 wherein the filaments are cylindrical.

7. A surgical clamp according to claim 4 wherein the filaments have at least three sides.

8. A surgical clamp according to claim 4 wherein the filaments have tip shapes, said tip shapes selected from the group consisting of rounded, semi-rounded angled-cut, blunt-cut or pointed.

9. A surgical clamp according to claim 8 wherein said tip shapes are rounded.

10. A surgical clamp according to claim 1 wherein said jaws have distal ends and the filaments extend in directions which resist movement of a vessel or other tissue engaged thereby towards the distal ends of the jaws.

11. A surgical clamp according to claim 1 wherein said jaws have distal ends and proximal ends and the filaments extend in directions which resist movement of a vessel or other tissue engaged thereby towards both said distal and proximal ends of the jaws.

12. A surgical clamp according to claim 1 wherein said jaws have distal ends, proximal ends, and a length therebetween, and the filaments extend in directions which resist movement of a vessel or other tissue engaged thereby along a direction transverse to said length.

13. A surgical clamp according to claim 10 wherein said resilient filaments are mounted on the opposed surface of at least one of said jaws, the opposed surface defining a plane having a longitudinal axis oriented parallel to the jaws and a normal axis extending perpendicularly from the plane, and wherein a group of said filaments extends at an angle from the opposed surface in a plane defined by the longitudinal axis and the normal axis.

14. The surgical clamp of claim 13 wherein said angle is between 30 to 60 degrees.

15. A surgical clamp according to claim 10 wherein said resilient filaments are mounted on the opposed surface of at least one of said jaws, the opposed surface defining a plane having a longitudinal axis oriented parallel to the jaws, a perpendicular axis within the plane and oriented perpendicular to the longitudinal axis, and a normal axis extending from the plane oriented perpendicular to both the longitudinal axis and the perpendicular axis, and wherein a first group of said filaments extends at a first angle from the opposed surface in a plane defined by the longitudinal axis and the normal axis, and a second group of said filaments extends at second angle from the opposed surface in a plane defined by the perpendicular axis and the normal axis.

16. The surgical clamp of claim 15 wherein said first and second angles are between 30 to 60 degrees.

17. A surgical clamp according to claim 15 wherein a third group of said filaments extends at a third angle from the opposed surface in a plane defined by the perpendicular axis and the normal axis in a direction opposed to the direction of said second group of said filaments relative to the perpendicular axis.

18. The surgical clamp of claim 17 wherein said third angle is between 30 to 60 degrees.

19. A surgical clamp according to claim 10 wherein said resilient filaments are mounted on the opposed surface of at least one of said jaws, the opposed surface defining a plane having a longitudinal axis oriented parallel to the jaws, a perpendicular axis within the plane oriented perpendicular to the longitudinal axis, and a normal axis extending from the plane oriented perpendicular to both the longitudinal axis and the perpendicular axis, and wherein a first group of said filaments extends at a first angle from the opposed surface in a first plane defined by the normal axis and a first axis parallel to the plane of the opposed surface, and a second group of said filaments extends at a second angle from the opposed surface in a second plane defined by the normal axis and a second axis parallel to the plane of the opposed surface, and said first axis and said second axis intersect to form an intersection angle less than 180 degrees.

20. The surgical clamp of claim 19 wherein said first and second angles are between 30 to 60 degrees.

21. A surgical clamp according to claim 2 wherein said opposed surface of at least one of said jaws comprises resiliently deflectable material.

22. A surgical clamp according to claim 21 wherein said resiliently deflectable material comprises silicone.

23. A surgical clamp according to claim 11 wherein the opposed surface of at least one of said jaws comprises resiliently deflectable material for engagement with said vessel or other tissue when said jaws are moved toward one another.

24. A surgical clamp according to claim 23 wherein the opposed surface of at least one of said jaws comprises silicone.

25. A surgical clamp according to claim 23 wherein said filaments comprise a first group and a second group of filaments, said first group having filaments oriented parallel to one another and said second group having filaments oriented parallel to one another and at an angle relative to the filaments of said first group.

26. A surgical clamp according to claim 25 wherein said angle between filaments of said first and second groups is a right angle.

27. A surgical clamp according to claim 25 wherein the opposed surface of at least one of said jaws defines a first plane and said first and second groups of filaments define a second plane, and wherein said first and second planes intersect to form an angle between 45–90 degrees.

28. A surgical clamp according to claim 27 wherein said angle of intersection is 45 degrees.

29. A surgical clamp according to claim 27 wherein said filaments terminate at a position below said first plane.

30. A surgical clamp according to claim 27 wherein said filaments terminate at a position above said first plane.

31. A surgical clamp according to claim 25 wherein said jaws further comprise a clamping member, said clamping member comprising means for attaching the clamping member to the jaws; and a clamp pad secured to said means wherein said clamp pad includes said opposed surface.

32. A surgical clamp according to claim 31 wherein said means is a rigid member and said filaments are mounted between the rigid member and said clamp pad.

33. A surgical clamp according to claim 31 wherein said means is a rigid member and said filaments are mounted on the rigid member.

34. A surgical clamp according to claim 31 wherein said clamp pad has an upper and a lower portion and said filaments are mounted between the upper and lower portions.

* * * * *